United States Patent [19]

Kronvall et al.

[11] Patent Number: 4,948,874

[45] Date of Patent: Aug. 14, 1990

[54] PURIFIED PROTEIN G FROM STREPTOCOCCAL BACTERIA

[75] Inventors: Goran Kronvall, Lund; Lars Bjorck, Sodra Sandby, both of Sweden

[73] Assignee: Pharmacia AB, Upsala, Sweden

[21] Appl. No.: 311,446

[22] Filed: Feb. 15, 1989

Related U.S. Application Data

[63] Continuation of Ser. No. 9,568, Jan. 30, 1987, abandoned, which is a continuation of Ser. No. 619,820, Jun. 12, 1984, abandoned.

[30] Foreign Application Priority Data

Aug. 20, 1984 [SE] Sweden ................................ 8303578

[51] Int. Cl.$^5$ ..................... C07K 15/04; C07K 3/12; C07K 15/00; C12P 21/00
[52] U.S. Cl. ................................. 530/350; 435/68.1; 435/71.1; 435/272; 435/820; 530/820; 530/825
[58] Field of Search ............... 435/69, 180, 257, 267, 435/272, 820, 68.1, 71.1; 530/825, 820, 350

[56] References Cited

U.S. PATENT DOCUMENTS

3,850,798 11/1974 Sjoquist ............................ 435/180 X
4,481,294 11/1984 Downs ................................ 435/259

OTHER PUBLICATIONS

Swanson et al., J. Exp. Med., vol. 130, 1969, pp. 1063-1091.
Lancefield, R. C., J. Immunol., vol. 89, 1962, pp. 307-313.
Hill, R. L., Advan. Protein Chem., vol. 20, 1965, pp. 37-107.
Myhre et al., Infection and Immunity, Sep. 1977, pp. 475-482.
Kronvall, G. The Journal of Immunology, vol. 111, No. 5, 1973, pp. 1401-1406.
Christensen et al., Acta. Path. Mircobiol. Scand. Sect. vol. 84, 1976, pp. 196-202.
Bjorck et al., "Purification and Some Properties of Streptococcal Protein G, a Novel IgG Binding Reagent", J. Immunol, 133 (2) (1984), pp. 969-974.

*Primary Examiner*—David M. Naff
*Attorney, Agent, or Firm*—Lowe, Price, LeBlanc, Becker & Shur

[57] ABSTRACT

A process is disclosed for recovering a cell wall protein, particularly a Fc-receptor, from streptococcal bacteria. In the process, streptococcal bacteria are treated with at least one proteolytic enzyme to solubilize the cell wall protein. A process is also disclosed for recovering Fc-receptor type III (protein G) having selective IgG-binding capability (i.e., no albumin-binding capability) from streptococcal bacteria by pretreating these bacteria with enzymes prior to said enzymatic solubilization.

1 Claim, No Drawings

PURIFIED PROTEIN G FROM STREPTOCOCCAL BACTERIA

This is a continuation of application Ser. No. 009,568 filed Jan. 30, 1987, which is a continuation of appln. Serial No. 619,820 filed on June 12, 1984, both now abandoned.

BACKGROUND OF THE INVENTION

This invention relates to a process for recovering a cell wall protein from streptococcal bacteria. More particularly, the invention relates to a process for recovering a Fc-receptor from such bacteria.

Fc-receptors from bacteria and processes for recovering these are known and described in the literature. For example, U.S. Pat. No. 3,850,798 describes a process for recovering the Fc-receptor protein A from staphylococcal bacteria through enzymatic solubilization using the enzyme trypsin.

A similar process using fag-induced cell wall-decomposing enzyme has also been suggested for solubilization of Fc-reactive protein from group A streptococci. This latter process constitutes one example of the principle that, by decomposing the long sugar polymers and the cross-linking peptide-bridges in the cell wall, a solubilization of all substances which were bonded to this structure will result. Residues of the cell wall may be left on the solubilized molecules. Simultaneously with the solubilization, all soluble intracellular substances from the streptococcal bacteria are released in the obtained liquid, which therefore will be very complex.

The former process, which according to U.S. Pat. No. 3,850,798 can be used in connection with staphylococcal bacteria, is a more selective process. However, such process according to our knowledge has neither been used nor described in connection with streptococcal bacteria. On the contrary, such use with streptococcal bacteria should have been deemed to be non-operative in view of the results which presently are known with respect to the protein nature of Fc-receptors and the sensitivity of these surface structures to proteolytic treatment. As a rule, a complete degradation of the proteins to amino acids and peptides are obtained, and all biological activity is lost.

SUMMARY OF THE INVENTION

It has now been surprisingly found in accordance with the present invention that streptococcal bacteria can be treated with proteolytic enzyme to solubilize cell wall protein. In particular, it has been found by the present invention that solubilized Fc-receptor type III (designated below as protein G) can be recovered from such treated bacteria.

Fc-receptors such as protein A and protein G have useful characteristics, for example the ability to bind to the Fc-portion of immunoglobulins. Fc-receptors can thus be advantageously be used as well as therapeutic as in analytical connections. One example of such a useful application is extra-corporeal treatment of blood in connection with some autoimmune diseases, wherein the Fc-receptor could be used as an agent to remove so-called immune complexes from the blood. In comparison to protein A, protein G has however several advantages which make protein G far superior. For example, protein G can bind to all IgG-subclasses, while protein A cannot bind to human IgG III. Furthermore, protein G lacks the ability to bind IgA and IgM. Thus, protein G is in a sense a more selective Fc-receptor than protein A, which binds also to these immunoglobulin classes.

According to our present knowledge, no simple process exists for recovering Fc-receptors, particularly protein G, from streptococcal bacteria. The need to find such a process therefore is great.

DETAILED DESCRIPTION OF INVENTION

The present invention provides a process for recovering a cell wall protein from streptococcal bacteria. The streptococcal bacteria are treated with a proteolytic enzyme to solubilize the cell wall protein. The solubilized cell wall protein is preferably isolated from the treatment suspension.

Suitable proteolytic enzymes that can be employed in the process of the invention include papain, trypsin and/or pepsin. Papain is a preferred enzyme.

As already mentioned, the recovered Fc-receptor from streptococcal bacteria can bind to all IgG-classes. Experiments have shown that the Fc-receptor (protein G) also bind to albumin which is a useful protein in blood plasma. This means that a competition between IgG and albumin to the binding surface on protein G thus can exist, when protein G is used in connection with an extracorporeal treatment of blood to remove immune complexes, as previously mentioned.

According to the invention, it has also been found that a still more selective protein G, i.e. a protein G which binds only to IgG but not to albumin, can be obtained from streptococcal bacteria. Such more selective protein G is obtained from bacteria which are exposed to an enzymatic pretreatment prior to the solubilization. This enzymatic pretreatment also preferably employs proteolytic enzymes. Preferred pretreatment enzymes include trypsin and/or pepsin.

The solubilized cell wall protein can be isolated and recovered in the way as described in the European Patent Publication No. 0 046 915. Briefly, in this known method the solubilized protein, possibly after filtration of bigger impurities, is brought into contact with a ligand having affinity to said protein to form a complex. The ligand is immobilized on a soluble carrier. The complex is then purified from possible similar impurities and thereafter split to release the protein. The released protein is then separated and recovered through filtration. For further details of this known method, reference is made to said European patent publication, the disclosure of which is incorporated herein in by reference.

A similar method, which can also be used according to the present invention, is described in U.S. patent application Ser. No. 07/129,935, filed Dec. 3, 1987, now U.S. Pat. No. 4,783,264, in the names of Nylen et al., the disclosure of which is incorporated herein by reference.

An effective amount of the enzyme is employed to solubilize the desired protein. Also, the enzymes employed in the process of the invention are preferably used in the form of a suspension. Preferably, the enzyme suspensions contain between about 50 and about 250 $\mu$g., preferably from about 75 to about 150 $\mu$g., enzyme per ml of a 10% bacteria suspension.

The following examples are presented for purposes of demonstrating, but not limiting, the process of the invention.

EXAMPLE 1

Human group G streptococcal bacteria, G 148, cultured in Tood/Hewitt-broth, were suspended (10% suspension) in 0.01M tris-HCl, pH 8.0. One hundred μl 0.4M L-cystein and 10 μl papain of varying concentration in the same buffer were added per ml bacterial suspension. The mixture was incubated for 1 hour at 37° C. Jodoacetamide was added to provide a final concentration of 6 mM and a bacterial suspension was obtained.

The so obtained bacterial suspension was centrifugated (2000 g) for 30 minutes. Thereafter, the supernatant was ultracentrifugated (50000 g), frozen immediately at −80° C., and used as starting material for isolation of the protein through sequential use of ion exchange chromatography on DEAE-cellulose gel, gel filtration on Sephadex G-100 and affinity chromatography on Sepharose 4B-bonded IgG.

The isolated protein migrated as a homogeneous band when analysed on SDS-PAGE. Also, on agarose gel electrophoreses only one band was seen in the alfa$_1$-region, indicating a high degree of purity.

SDS-PAGE in disks and in rods (labeled protein G) both gave an apparent molecular weight of 30500. Treatment of the protein with 2-mercaptoethanol did not influence the result.

EXAMPLE 2

0.5 mg pepsin is added per ml of 10% bacterial suspension (streptococcal bacteria of the same kind as in Example 1 above) in 0.1M acetate buffer, ph 4.0μ and was incubated for 30 minutes at 37° C. Tests according to known methods on the remaining bacterial bodies showed that they completely lacked the ability to bind albumin, while the ability to bind IgG was maintained unaffected.

These pepsin-pretreated bacteria were washed in 0.1M tris-HCl, pH 8.0, and diluted to a 10% suspension in this buffer. Thereafter, the enzmatic solubilization with papain was performed in the same way as described above in Example 1 to recover a protein G having the ability to selectively bind IgG.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A purified Protein G having the ability to bind to all IgG subclasses while lacking the ability to bind IgA and IgM and not binding to albumin, said Protein G exhibiting only one band in an alfa-region on agarose gel electrophoresis and not being reduced by 2-mercaptoethanol.

* * * * *

UNITED STATES PATENT AND TRADEMARK OFFICE
CERTIFICATE OF CORRECTION

PATENT NO. : 4,948,874

DATED : August 14, 1990

INVENTOR(S) : Kronvall et al.

It is certified that error appears in the above-identified patent and that said Letters Patent is hereby corrected as shown below:

On the title page:

Under [30] Foreign Application Priority Data, change "Aug. 20, 1984" to --June 22, 1983--.

Signed and Sealed this

Eighteenth Day of June, 1991

Attest:

HARRY F. MANBECK, JR.

*Attesting Officer*            *Commissioner of Patents and Trademarks*